(12) United States Patent
Hussam et al.

(10) Patent No.: US 10,964,432 B2
(45) Date of Patent: Mar. 30, 2021

(54) PROCESSING OF PORTABLE DEVICE DATA

(71) Applicant: Universal Research Solutions, LLC, Columbia, MO (US)

(72) Inventors: Ali Adel Hussam, Columbia, MO (US); Nathan Bleigh, Kansas City, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 1164 days.

(21) Appl. No.: 15/008,296

(22) Filed: Jan. 27, 2016

(65) Prior Publication Data

US 2017/0199972 A1  Jul. 13, 2017

Related U.S. Application Data

(63) Continuation-in-part of application No. 14/991,379, filed on Jan. 8, 2016, now Pat. No. 10,103,947.

(51) Int. Cl.
*G16H 40/67* (2018.01)
*A61B 5/00* (2006.01)
*G16H 10/60* (2018.01)
*G16H 10/20* (2018.01)

(52) U.S. Cl.
CPC ........... *G16H 40/67* (2018.01); *A61B 5/0022* (2013.01); *G16H 10/60* (2018.01); *G16H 10/20* (2018.01)

(58) Field of Classification Search
CPC .............................................. G06Q 50/22–24
See application file for complete search history.

(56) References Cited

U.S. PATENT DOCUMENTS

| | | | |
|---|---|---|---|
| 8,812,259 B2 | 8/2014 | Messenger et al. | |
| 2007/0288067 A1 | 12/2007 | Eveland | |
| 2015/0088007 A1 | 3/2015 | Bardy et al. | |
| 2015/0207915 A1 | 7/2015 | Roberts et al. | |
| 2015/0272501 A1* | 10/2015 | Maceachern | ........ A61B 5/0531 600/301 |
| 2017/0161452 A1* | 6/2017 | Bain | ................... G06F 19/3481 |

OTHER PUBLICATIONS

Transmittal of International Search Report and Written Opinion in corresponding PCT Application No. PCT/US2017/012746, dated Mar. 16, 2017, pp. 1-7.

* cited by examiner

*Primary Examiner* — Robert A Sorey
(74) *Attorney, Agent, or Firm* — Fish & Richardson P.C.

(57) ABSTRACT

A method for processing data in a data processing system, the method comprising: receiving, by the data processing system, portable device data collected by a portable device; determining, by a first data processing program of the data processing system, one or more characteristics of the portable device data; based on the one or more characteristics, selecting, by the data processing system, prompt data for transmission to a client device; and causing, by the data processing system over one or more networks, the prompt data to be transmitted to the client device.

23 Claims, 7 Drawing Sheets

PROCESSING OF PORTABLE DEVICE DATA

CLAIM OF PRIORITY

This application is a continuation-in-part of and claims priority under 35 U.S.C. § 121 to U.S. patent application Ser. No. 14/991,379, filed Jan. 8, 2016, the entire contents of which are hereby incorporated by reference.

BACKGROUND

There are various types of portable devices, including, e.g., activity trackers, wireless-enabled wearable technology devices that measure data such as the number of steps walked, quality of sleep, steps climbed, and other metrics.

SUMMARY

In some examples, a computer-implemented method comprises receiving portable device data collected by a portable device; determining, by a first data processing program of the data processing system, one or more characteristics of the portable device data; based on the one or more characteristics, selecting prompt data for transmission to a client device; and causing, by over one or more networks, the prompt data to be transmitted to the client device. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In some examples, the operations further comprise: filtering data representing candidate prompt data by removing one or more items candidate prompt data that are unassociated with the one or more characteristics; from among the filtered data, selecting an item of prompt data; generating the alert from the filtered, selected data, with the alert comprising a universal resource locator (URL), which specifies a location of a system for activating or viewing the selected prompt data; wherein causing the prompt data to be transmitted comprises transmitting the alert over a wireless communication channel to a wireless device associated with the user based upon a destination address of the wireless device; wherein the alert activates a viewer application to cause the alert to display on the wireless device and to enable connection via the URL to the system over the Internet when the wireless device is online. The operations further comprise: generating a push notification for transmitting the alert to the client device. The operations further comprise: binding values of one or more attributes included in the portable device data to one or more parameters of a rules engine; applying one or more rules to the bound parameters; and based on application of the rules, selecting the prompt data for transmission. The portable device data is received from a third party system.

Causing the prompt data to be transmitted comprises transmitting the prompt data to a third party system for transmission to the portable device. The operations further comprise: responsive to the prompt data, receiving outcomes data. The operations further comprise: updating one or more entries in a data registry with the received outcomes data. The operations further comprise: applying one or more rules to the received outcomes data; and generating an outcomes score. The operations further comprise: retrieving one or more of demographics data, satisfaction data, procedure data and implant for a user associated with the outcomes data; based on the retrieved data and the received outcomes data, determining an assessment of medical care for the user. The portable device comprises a wearable device. The operations further comprise: receiving consolidated clinical document architecture (CCDA) data from one or more external systems; parsing the CCDA data to identify data associated with one or more predefined attributes; identifying one or more users associated with the identified data; and for the one or more identified users, identifying one or more portions of wearable device data pertaining to the one or more identified users, with the one or more portions of wearable device data specifying one or more specified characteristics of interest. The operations further comprise: generating data for a graphical user interface that when rendered on a display device, renders a unified data visualization by displaying: a first visualization of outcomes data over a specified time range; a second visualization of patient defined outcomes data over the same specified time range; and a third visualization of wearable metrics data over the same specified time range, with the first, second and third visualizations each being juxtaposed to each other.

All or part of the foregoing may be implemented as a computer program product including instructions that are stored on one or more non-transitory machine-readable storage media and/or one or more machine-readable hardware storage devices that are executable on one or more processing devices. All or part of the foregoing may be implemented as an apparatus, method, or electronic system that may include one or more processing devices and memory to store executable instructions to implement the stated functions.

The details of one or more embodiments are set forth in the accompanying drawings and the description below. Other features, objects, and advantages of the techniques described herein will be apparent from the description and drawings, and from the claims.

DETAILED DESCRIPTION

Figure 1:
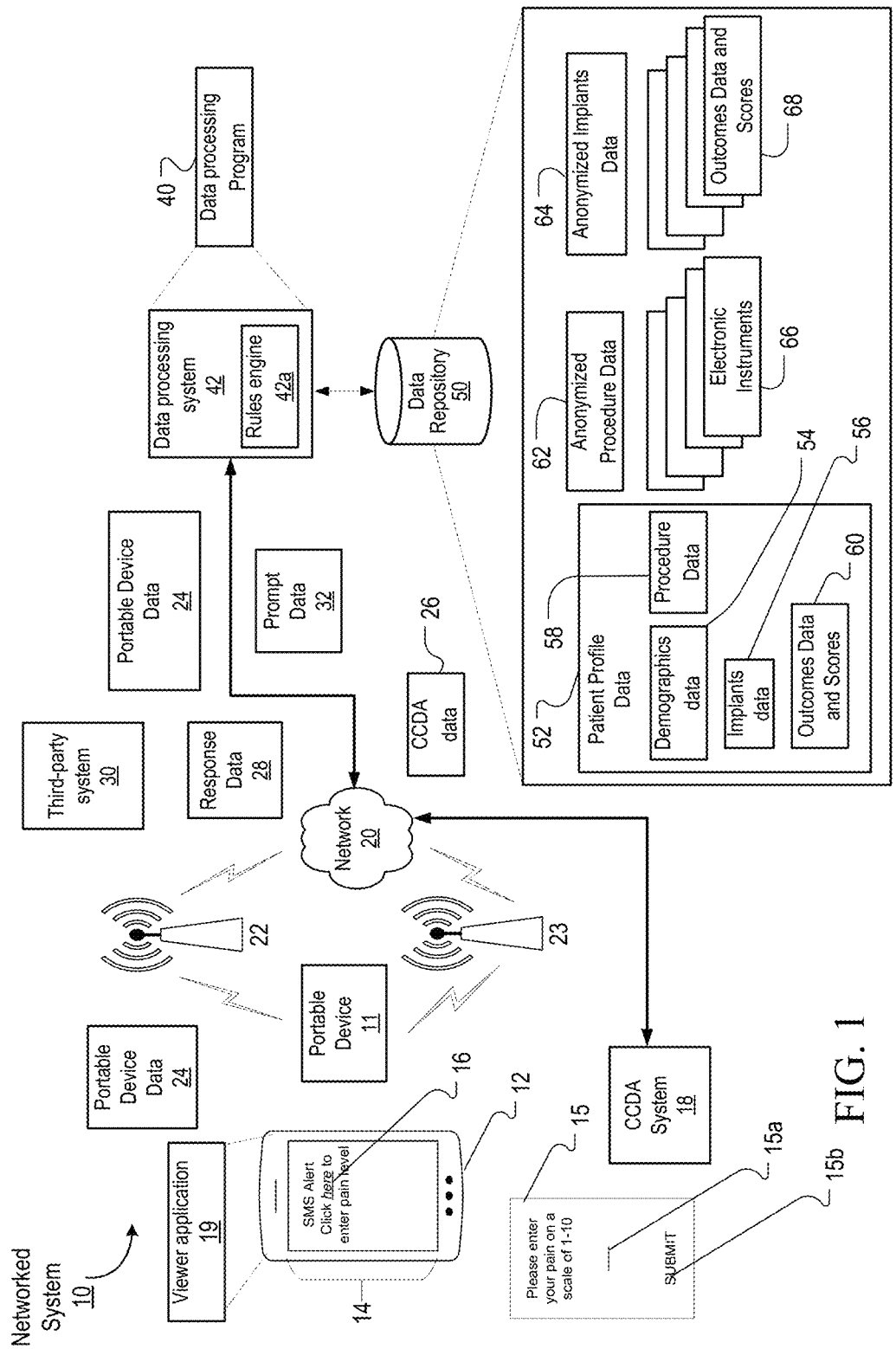
FIG. 1 shows a diagram of an example of a networked data processing system for processing portable device data.

FIG. 1 is a diagram which shows an example of a networked system 10 for processing portable device data 24. The networked system 10 includes a portable device 11, a client device 12, a network 20, wireless devices 22, 23, a Consolidated Clinical Document Architecture (CCDA) system 18, a data processing system 42, and a data repository 50. In some examples, the networked system can include a third-party system 30. Portable device data 24 can be transmitted from the portable device 11 using one or more of the wireless devices 22, 23 and the network 20. In some examples, the CCDA system 18 can transmit CCDA data 26 to the data processing system 42. The data processing system 42 can analyze the portable device data 24 using a data processing program 40 and produce prompt data 32. Generally, prompt data includes data that prompts a user to input information (e.g., by answering questions), that prompts a user to perform one or more actions, and so forth. The data processing system 42 can transmit the prompt data 32 to a client device 12. The client device 12 can transmit response data 28 to the data processing system 42. The response data 28 can be stored in the data repository 50 for further use. Generally, data is stored in data repository 50 as one or more data records. Data in data repository 50 is updated by updating or modifying the underlying data records.

An overview of the networked system 10 is as follows. The portable device 11 can collect portable device data 24 related to the activity of the patient. The portable device 11 can transmit the collected portable device data 24 using one or more of the wireless devices 22, 23 and the network 20 to the data processing system 42. In some examples, the portable device 11 transmits the portable device data 24 to the third-party system 30 using the wireless devices 22, 23. The third-party system 30 can transmit received portable device data 24 to the data processing system 42, such as when the data processing system 42 makes a request for the portable device data 24 received by the third-party system 30. In some examples, the CCDA system 18 can provide CCDA data 26 to the data processing system 42 using the one or more of the wireless devices 22, 23, and the network 20. The data processing system 42 can analyze the portable device data 24 using the data processing program 40. A rules engine 42*a* can be used by the data processing program 40. The data processing system 42 can communicate with the data repository 50. The data processing program 40 can make a determination that prompt data 32 should be transmitted by the data processing system 42 using the network 20 to the client device 12. This determination can be based on one or more of the portable device data 24, the CCDA data 26, and data stored in the data repository 50, such as patient profile data 52, anonymized procedure data 62, anonymized implants data 62, outcomes data and scores 68, electronic instruments data 66, or other data stored in the data repository 50. Once the rules engine 42*a* has made a determination that prompt data 32 should be transmitted, the data processing system 42 transmits the prompt data 32 using one or more the wireless devices 22, 23 and the network 20 to the client device 12. The client device 12 is used by a user, such as a patient, to receive the prompt data 32. The patient can view the prompt data 32 using a user interface 14 of the client device 12. The prompt data 32 can include an instruction 16. The patient can generate response data 28 by responding to the instruction 16. The response data 28 can be analyzed by the data processing system 42. The response data 28 can be stored in the data repository 50 for further use.

A user of the networked system 10 can include a patient, such as a person who is using the portable device 11, in some contexts. The patient can be someone having undergone a medical procedure such as a surgery, medical examination, medical test, therapy, checkup, physical, or other such medical procedure. The patient can be someone who is using the portable device 11. The patient can be someone who is using the client device 12.

The user of the networked system 10 can include a medical service provider, such as a physician or hospital representative using or analyzing the data in the data repository 50, in other contexts. The medical service provider can be an entity which generated, assigned, or designed prompt data 32.

The portable device 11 can be used to collect data for the networked system. The portable device 11 can include a computer processor, one or more sensors which can gather data, and a means for transmitting data using one or more of the wireless devices 22, 23 and the network 20. In some examples, the portable device 11 can store portable device data 24 using a means for storing data such as solid state storage, a hard drive disk, or other storage device, for later transmission. The portable device 11 can be portable such that a patient can carry the portable device. In some examples, the portable device 11 can be a mobile communication device, such as a smartphone. In some examples, the portable device 11 can be worn by the patient. Some examples of a wearable device include Fitbit produced by Fitbit of San Francisco, Calif.; smartwatches such as the Apple Watch produced by Apple of Cupertino, Calif.; and similar devices.

The portable device 11 can be used to monitor activity, such as physical activity, of the patient and gather portable device data 24 relating to the activity of the patient. The portable device data 24 includes one or more characteristics. The characteristics of the portable device data 24 include the type of measurement of patient activity, such as a number of steps taken by the patient; a distance the patient has run walked, jogged, or the like; a heartrate of the patient; approximate calories burned by the patient; sleep patterns of the patient; a number of stairs climbed by the patient; or other data representing activity by the patient. The characteristics of the portable device data 24 include the values of the data. The characteristics of the portable device data 24 can include an identifier relating the measurements of patient activity to a particular patient. The portable device data 24 includes an identifier of the portable device 11 which associates it with a patient. The identifier can be used during analysis by the data processing program 40 to identify the patient. The identifier can be used for associating the portable device data 24 with the proper patient profile data 52 in the data repository 50. In some examples, the portable device 11 can transmit data wirelessly using one or more of the wireless devices 22, 23 and the network 20. In some examples, more than one portable device 11 can be used to monitor activity and gather portable device data 24. In some examples, the portable device 11 can be the client device 12.

The network 20 can be used to transmit data from one device to another in the networked system 10. The network 20 can include wired communications links and wireless communications links. The communications links can use network protocols such as TCP/IP, Bluetooth °, Ethernet, or other network protocols. The communications links can use communication protocols such as HTTP, IMAP, POP, or other communication protocols. In some examples, the communications links can use one or more of SMS and IVR messaging communication standards.

The network 20 can include wireless devices 22, 23. Wireless devices 22, 23 include Wi-Fi routers, Wi-Fi access points, wireless tracking devices, beacons, computing devices, laptops and so forth. In some examples, wireless devices 22, 23 include cellular networks such as LTE networks. Wireless devices 22, 23 can communicate via the network 20 to the networked system 10 and also communicate with the client device 12, the portable device 11. In some examples, the wireless devices can communicate via the network 20 to the third-party system 30, the data processing system 42, and the CCDA system 18. In some examples, wireless devices 22, 23 are fixed location wireless devices, such as fixed location routers or computers. In other examples, wireless devices 22, 23, are discoverable (e.g., by the networked system 10), when one or more of wireless devices 22, 23 are connected to a network or connected to a port.

In some examples, the third-party system 30 can be connected using the network 20. The third-party system 30 can be a device, such as a server, which can receive the portable device data 24 from portable device 11. The portable device 11 is configured to automatically transmit portable device data 24 to the third-party system 30 which can then store the portable device data 24 for later use, such as transmission to the data processing system 42. The third-party system 30 can be configured to receive and process the portable device data 24. In some examples, the portable device data 24 can be accessed from the third-party system 30 using an application program interface (API) associated with the third-party system 30. In some examples, the third-party system 30 is a server associated with the manufacturer of the portable device 11. In some examples, access to the third-party system 30 requires a permission such as the consent of the patient. The consent of the patient can be obtained using a clinician web portal of the medical service provider or using a patient web portal over the Internet. The permission can be obtained in advance of gathering or measuring the portable device data 24. In some examples, the permission can be obtained by registering the portable device 11 with the networked system 10. In some examples, the permission can be obtained by electronic consent. In some examples, the third-party system 30 can passively (i.e., without manipulation) forward the portable device data 32 to the data processing system 42.

In some examples, the Consolidated Clinical Document Architecture (CCDA) system 18 can be connected using the network 20. The CCDA system can be a device, such as a server, which can receive and store CCDA data 26 and transmit CCDA data 26 to the data processing system 42. The CCDA system 18 stores clinical data in a standardized format suitable for a Health Information Exchange (HIE). In some examples, the CCDA data 26 can be accessed from the CCDA system 18 using an application program interface (API) associated with the CCDA system 18. In some examples, CCDA system 18 is a server associated with the medical service provider and/or a medical entity.

The CCDA data 26 conforms to the CCDA and can include CCDA documents. The CCDA can standardize the content and structure for clinical care summaries by using predefined attributes. CCDA documents are coded in XML, and XHTML. CCDA documents can include a header which enables exchange of clinical documents within and across institutions. CCDA documents include a patient identifier. CCDA documents can include a body which includes the clinical report and one or more sections, such as allergies of a patient, medicine used, vital signs, immunizations, and the like. The body can include a narrative block. The body can include machine readable entries. The data processing system 42 can use one or more CCDA patient identifiers to identify a number of patients associated with an attribute of interest in the CCDA documents. The data processing system can determine which portable device 11 associated with the identified patients and the associated characteristic of interest in the portable device data 24.

Figure 7:
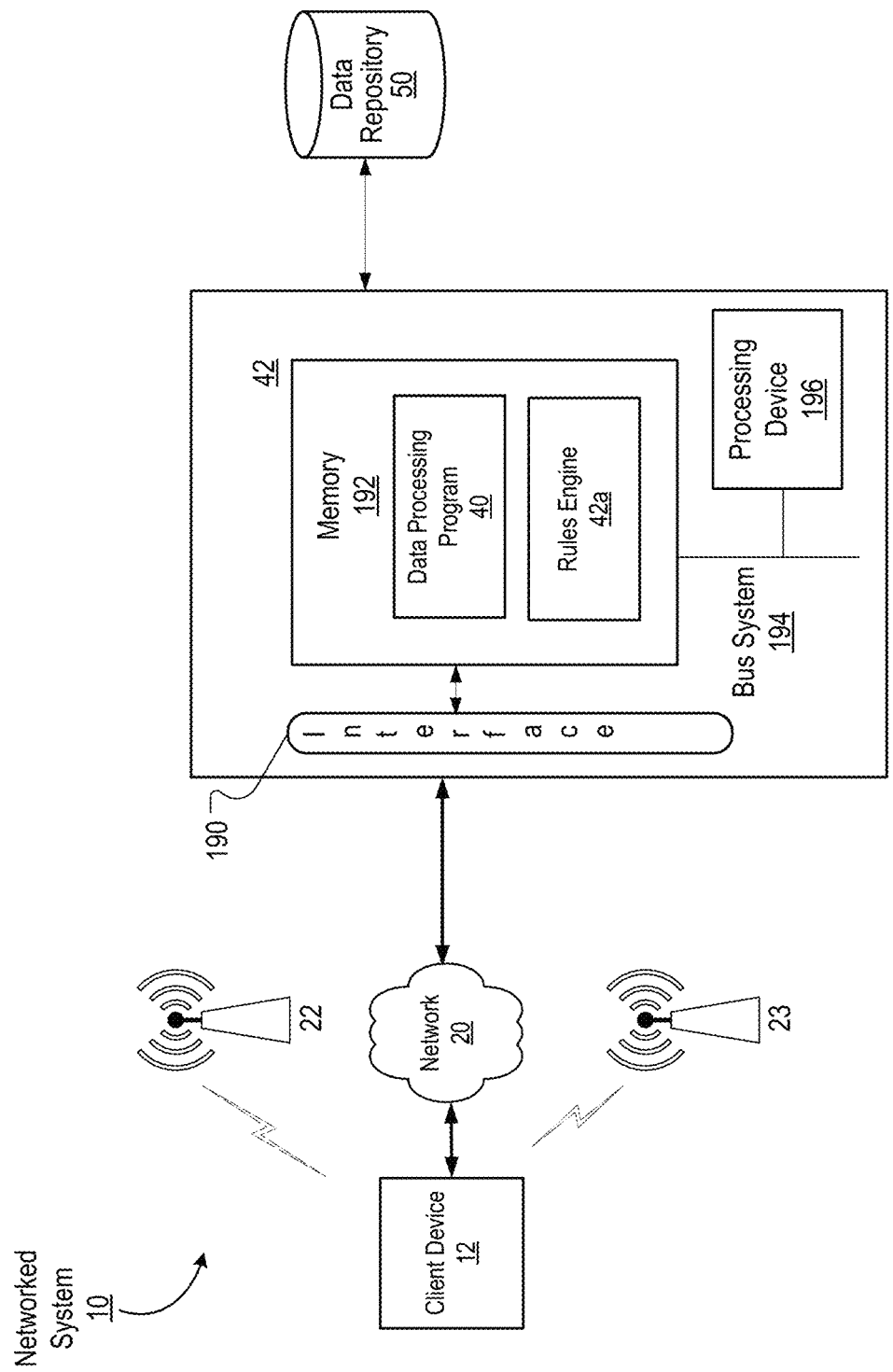
FIG. 7 is a block diagram showing components of the system for processing portable device data.

The data processing system 42 is connected to the network 20 and can include a processing device 196, a rules engine 42a, and other components described in more detail with respect to FIG. 7. The data processing system 42 can receive data from the network 20. Portable device data 24 can be received by the data processing system 42. The data processing system can analyze the portable device data 24 using a data processing program 40 as described in more detail in relation to FIG. 5. Using the rules engine 42a, the data processing system 42 can determine the patient's identity by analyzing the portable device data 24. The data processing system 42 can filter data representing candidate prompt data by removing one or more items of prompt that are unassociated with one or more characteristics of the portable device data 24, e.g., based on matching of characteristics or attributes. In an example, each item of prompt data is associated with one more attributes. In this example, data processing system compares attributes of portable device data 24 to attributes of items of prompt data 32. Based on matches or correspondences, data processing system 42 identifies one or more items of prompt data 32 to be transmitted to client device 12 (or to portable device 11). The data processing system 42 can select which of the filtered prompt data 24 to transmit based on the one or more characteristics of the portable device data 24. In some examples, the data processing system 42 can bind values of one or more attributes included in the portable device data 24 to one or more parameters of the rules engine 42a.

For example, the rules engine 42a includes the follow rule:

When X>5000, then send prompt data for pain entry

In this example, X is a parameter representing the number of steps a user has walked. The portable device data includes the following attribute: walked steps=2500. In this example, data processing system 42 binds the value (2500) of the "walked steps" attribute to parameter X, thereby setting the value of parameter X to be 2500. In this example, the condition precedent (X>5000) of the rule is not satisfied. Accordingly, the rules is not executed to cause the prompt data to be sent.

The data processing system 42 can apply the one or more rules to the bound parameters, and based on the application of the rules, select prompt data for transmission. For example, if the number of steps the patient took exceeds a trigger threshold, the associated prompt data 24 can be selected. The data processing system 42 can determine by analyzing the portable device data 24 whether prompt data 32 should be transmitted to the client device 12 using the network 20. The data processing system communicates with the data repository 50 which can be used to store data for analysis by the data processing system 42. In some examples, the data processing system can receive response data 28 from the client device 12. The response data 28 can be stored in the data repository 50 for later use or analyzed as described in relation to FIGS. 2-3, and 6. In some examples, the data processing system 42 can receive CCDA data 26 from the CCDA system 18. The CCDA data 26 can be stored in the data repository 50 for later use or analyzed as described in relation to FIGS. 2-3, and 6.

The data repository 50 stores data which can be used by the networked system 10, including the data processing system 42. The data repository 50 can store patient profile data 52 for a number of patients. The patient profile data 52 can be a data registry. The patient profile data 52 includes relevant information about the patient who is using the networked system 10 and transmit the patient profile data 52 to the data processing system 42. The patient profile data 52 includes demographics data 54, implants data 56, outcomes data and scores 60, and procedure data 58. Demographics data 54 includes information about the patient relating to the patient's medical history such as age, race, ethnicity, blood type, known allergies, known prior and current medications used by the patient, known current and prior diseases and family history of disease, records of prior activity, and the like. The procedure data 58 can include a record of prior and scheduled medical procedures for the patient, prior and current therapy and treatment regimes, and similar information. The implants data 56 can include a list of prior and current medical implants and medical devices used by the patient, such as prosthetics, braces, stents, or other implants and devices which the patient has used.

The outcomes data and scores 60 includes outcomes data provided by or on behalf of the patient. Outcomes data 60 includes, for example, results of a medical procedure and information related to therapy or treatment undergone by the patient. The outcomes data 60 can be provided to the data repository 50 in the form of response data 28 provided by the client device 12. The outcomes data can be entered into the patient profile data 52 by updating one or more entries in the data registry with the received outcomes data. In some examples, the patient may complete a standardized form by answering questions and rating his or her condition, such as pain experienced or other metrics, in a standardized format. The rating can be in the form of a numerical score. The outcomes data 60, 68 can be accessed by a physician or other medical service provider to monitor the progress, compliance, and efficacy of the therapy of the patient or a group of patients. The outcomes data can be associated with one or more of demographics data, satisfaction data, procedure data, and implant data of the patient profile data 52. The outcomes data can be used to determine an assessment of medical care for the patient, such as changing a prescribed therapy regime to increase efficacy, reduce injury, or other medical goals.

An outcomes score can be generated by applying one or more rules by the rules engine 42a to the outcomes data. The outcomes score can represent one or more metrics related to the medical care or activity of the patient. For example, the outcomes score can reflect adherence levels by the patient a prescribed therapy regime. In other implementations, the outcomes score can reflect the efficacy of a medical procedure. More detail on the outcomes data and scores 60, 68, is described in relation to FIG. 6.

An example of patient profile data 52 can be as follows. The patient may be a middle-aged woman aged fifty having undergone knee reconstruction surgery six months ago. The patient profile data 52 may include details of the treatment, such as the date of the procedure, the identity of a performing physician or other medical service provider, and any complications that occurred and how they were handled. The patient profile data 52 can include the details of the physical therapy prescribed by the medical service provider, such as requiring the woman to walk one mile each day. The patient profile data 52 can include details of a knee implant including the manufacturer and the model. The patient profile data 52 may include a record of outcomes data 60 provided by the woman such as a pain rating on a scale of 1-10 which records a pain level experienced at, for example, the time of completing her one mile walk each day. The woman can provide to the data repository by using in the form of response data 28 by using the client device 12 and the network 20. The data repository can store the response data 28 of the woman for each day that she completes her therapy and monitor compliance of the therapy, such as alerting the medical service provider when the therapy regime is not followed properly.

In some implementations it is desirable to store data using the data repository 50 without associating the data with a patient profile. The data repository 50 can store anonymized procedure data 62, anonymized implants 64, electronic instruments 66, and outcomes data and scores 68 for a number of patients. Generally, anonymized includes de-identified. For example, the anonymized procedure data 62 can include a record of many instances of a particular procedure, the demographics of patients for the procedure, which physicians or medical service providers performed the procedures, and the like. This anonymized procedure data 62 is used as an overlay in charting a patient's outcomes data, as described in further detail in FIG. 6. For example, data processing system 42 generates a chart with one plot representing a particular patients outcome (e.g., pain level or healing) for a particular procedure (e.g., as specified in procedure data 58 and/or outcomes data and scores 60) over a specified time period. Data processing system 42 generations another plot (for insertion into the same chart) representing outcomes (e.g., average outcomes) of a group of patients for the same procedure over the same time period (e.g., as specified in anonymized procedure data 62 and/or a portion of outcomes data and score 68 for that procedure).

The anonymized implants data 64 can include a record of the medical devices and implants used over a period of time for many kinds of procedures and patients. For example, data for an implant, such as a particular knee replacement, can be collected over a period of time for a large number of procedures and patients. In some examples, the anonymized implants data 64 can be associated with the outcomes data and scores 68 for a number of patients, which may include patients having many different demographics, such that the efficacy of the implant or medical device can be analyzed for the number of patients and/or the efficacy of an implant for a particular patient (e.g., as specified in implants data 56) can be compared to the efficacy across a whole group (e.g., as specified in anonymized implants data 64).

The data repository 50 can store data related to groups of patients. Electronic instruments data 66 can include a record of the client device 12 and the portable device 11 supported by the networked system 10 and the associated data required to interface with and analyze the data that these devices can provide in the form of the response data 28 and the portable device data 24. In another example, the electronic instruments data includes electronic forms (e.g., outcomes forms). In some examples, the portable device data 24 may be provided by the third-party system 30, which may provide data in a particular format or require certain permissions to access the data of the patient. The outcomes data and scores can include a list of outcomes from various procedures, ratings, and scores by provided by patients after procedures, during therapy, during treatment, or the like. This data is similar to the outcomes data and scores 60 but can include the aggregate records of many anonymous patients. For example, the outcomes data and scores 68 provided by patients for procedures performed at a particular hospital can be aggregated and analyzed. In some examples, the outcomes data and scores 68 provided by patients for a particular procedure can be aggregated and analyzed. In some examples, the outcomes data and scores 68 for a particular implant or medical device 64 can be aggregated and analyzed. The data stored in the data repository can be combined and analyzed in any combination to achieve a desired goal of a user of the networked system 10, such as a medical service provider.

Prompt data 32 can include information such as a message, instruction, question, alert, notification, form, or other such information. The prompt data 32 can be transmitted in the format of an SMS message, IVR message, email, push notification, or a similar format. In some examples, prompt data 32 includes an alert having a universal resource locator (URL) specifying a location of a system for activating or viewing the selected prompt data 32. A medical service provider can designate the conditions in which the data processing system 42 selects and transmits prompt data 32 to the client device 12 related to a particular patient. Once prompt data 32 has been selected by the data processing program 40, the prompt data 32 can be transmitted to the client device 12 based on the destination address of the client device 12.

The client device 12 can be used to receive the prompt data 32 from the data processing system 42. The client device 12 can include a computer processor, a means for receiving prompt data 32, a user interface 14, and a means for transmitting response data 28 using the network 20. The client device 12 can be a computer, mobile phone, tablet, laptop, or other such device, each of which may be a remote to system, 42. The client device 12 can be a wireless device which can connect to the Internet. In some examples, the client device 12 can be the same as the portable device 11. In some examples, the prompt data 32 can be received by more than one client device 12. The prompt data 32 can appear on the user interface as an instruction 16 (e.g., such as a selectable link or hyperlink, also referred to herein as hyperlink 16) in the form of a message, notification, question, alert, or other such instruction. In some examples, the prompt data 32 appears as a URL link specifying a location of a system for activating or viewing a prompt screen that displays one or more questions from electronic instruments 66 (or other questions or data). As described herein, electronic instruments 66 include outcomes form for collection of outcomes data. In this example, upon selection of hyperlink 16, client device 12 sends a request to data processing system 42 for one or more outcomes questions. In response to the request, data processing system 42 selects an appropriate question from an appropriate one of electronic instruments 66 and sends to client device 12 data (which may also be referred to as prompt data, as it prompts the user to input data) representing the selected question for rendering in graphical user interface 15. In this example, graphical user interface 15 includes input portion 15a for input of data responsive to the prompt. Graphical user interface 15 also includes submit control 15b to transmit the input data to data processing system 42 for storage in patient profile data 52. In this example, the input data includes response data 28.

Data processing system 42 selects an appropriate one of electronic instruments 66 based on various criteria, such as whether the user has had an implant and which one (as specified by implants data 56), whether the user has had a procedure and which one (as specified by procedure data 58) and user demographics (as specified by demographics data 54). In an example, rules engines 42a includes rules to select an appropriate one of electronic instruments 66 based on one or more of the foregoing criteria. Once an appropriate one of electronic instruments 66 is selected, data processing system 42 selects an appropriate question from that instrument. In some examples, the appropriate question is one that a physician specified should be displayed based on contents of portable device or is one that is previously unanswered by the user. In this example, following selection of hyperlink and when the client device 12 is online, the patient is able to activate the URL and connect to the networked system 10 over the Internet.

The client device 12 can be used to generate response data 28. The patient can use the user interface 14 of the client device 12 to respond to the prompt data 32 instruction 16 by, for example, activating a link, filling out a form, entering numerical or textual data, uploading a picture, uploading audio, or other forms of data entry. The response data 28 can be data transmitted by a patient which is responding to the prompt data 32. The response data 28 can include a completed form entry, audio, text, images, or numerical or textual information inputted by the patient to respond to the prompt data 32. The response data 28 includes a date of entry, time of entry, or both. The response data 28 can be transmitted using the network 20 to the data processing system 42. The response data 28 can be analyzed by the data processing system 42 and transmitted to the data repository 50 for later use. The response data 28 can be associated with the patient in the patient profile data 52. The response data 28 can include and identifier relating the responses to a particular patient. The identifier can be used during analysis by the data processing program 40 to identify the patient. The identifier can be used for associating the response data 28 with the proper patient profile data 52 in the data repository 50. The response data 28 can be stored anonymously. The response data 28 can include one or more of outcomes data and scores 60, 68.

In a variation of FIG. 1, networked system 10 distributes prompt data over a network to a remote subscriber computer (e.g., client device 12 or portable device 11). In this example, data processing system 42 provides viewer application 19 (for viewing of prompt data and/or graphical user interfaces, such as GUI 15) to a subscriber or user for installation on the remote subscriber computer. Data processing system 42 receives portable device data 24 sent from a data source (e.g., third party system) over the Internet. In this example, data processing system 42 includes a microprocessor and a memory that stores the remote subscriber's preferences for information format, destination address (e.g., of one or more of client device 12 and portable device 11), specified patient profile data 52, anonymized procedure data 62, electronic instruments data 66, outcomes data and scores 68, and so forth.

In this example, the microprocessor filters candidate prompt data (for transmission to the subscriber) by comparing the received portable device data 24 (or attributes thereof) to candidate prompt data (or attributes thereof). The microprocessor generates an alert (e.g., displayed in one of GUIS 14, 15 based on prompt data 32 or prompt data 32 itself) from the filtered candidate prompt data that contains an outcomes name, an outcomes prompt data and a universal resource locator (URL), which specifies the location of a data source (e.g., system 42) for viewing a resource (e.g., webpage rendered in GUI 14 or 15). The microprocessor also formats the alert into data blocks according to one or more of the information format, and transmits the formatted alert over a wireless communication channel to a wireless device (e.g., portable device 11 or another portable device or client device) associated with a subscriber based upon the destination address and/or a transmission schedule. After receiving the alert, the subscriber can connect the wireless device to the subscriber's computer. The alert causes the subscriber's computer to auto-launch the viewer application to view the alert. In this example, the alert activates the viewer application 19 (e.g., an application dedicated to communication with system 42) to cause the alert to display on the remote subscriber computer and to enable connection via the URL to the data source over the Internet when the wireless device is locally connected to the remote subscriber computer and the remote subscriber computer comes online. By doing so, a user is alerted to time sensitive information (e.g., time sensitive medical information to assess patient outcomes and detect a likelihood of a medical emergency or occurrence), even when the user's computer is offline, e.g., by transmitting the alert over a wireless communication channel to activate the viewer application, which causes the alert to display and enables the connection of the remote subscriber computer to the data source over the Internet when the remote subscriber computer comes online.

Additionally, the techniques described herein provide for improved processing speed and decreased latency of data processing system 42, because data processing system 42 can delete and remove (from memory and/or one or more data records in data repository) portable device data 24, following execution of one or more rules in rules engine 42*a* against portable device data 24, as portable device data 24 may be stored by third party system 30. In a variation, data processing system 42 receives portable device data 24 as a near-real time data stream and processes portable device data 24 as it is streamed in, independent of storing portable device data 24 in data repository 50. This results in faster processing speed and decreased latency as data processing system 42 does not need to query portable device data 24 from a data repository and can delete or purge portable device data 24 from memory or cache upon completion of processing and analyzing portable device data 24.

System 42 uses wearable devices to collect data (e.g., portable device data 24) which can be used to add to, and validate existing, patient-reported outcomes data (e.g., in outcomes data 60). In an example, a medical instrument or outcomes form is included in electronic instruments 66. System 42 automatically transmits these instruments 66 to patients, who answer the questions in the forms and transmit data indicative of these to system 42. Generally, in one embodiment, outcomes data includes these answers to these questions, because these answers are indicative of an outcome of a medical procedure or implant. Medical forms that include these questions regarding an outcome are outcome forms.

In this example, a patient who, while exercising, answers a question about their level of discomfort—which triggers a query real-time via text message to their provider. And that is accompanied by the vast amount of system-collected information—demographics, procedures, implant data and the question of overall satisfaction—to provide a complete picture of the individual's care at a particular hospital or institution that performed the procedure. In this example, system 42 generates charts and analyses for specifying a better understanding of the factors that influence health outcomes and provide more complete answers to the patient.

System 42 generates reports and analyses with a complete picture of the patient's outcomes after a procedure, adding another rich layer to the patient's data-set as stored in patient profile data 52. These reports include the patient's outcomes data juxtaposed to demographic data, procedures data and implants data to enable a view to assess correlations between the outcomes data and one or more of the demographic data, the procedures data and the implants data and various other types of data. System 42 compares reported outcomes (e.g., data indicative of range of motion following a procedure) in the outcomes data 66 with the objective data (e.g., data 24) captured by the wearable (e.g., from 3-D motion sensors), to verify and validate, and even update that outcomes data. For example, system 42 receives outcomes data (e.g., from a patient submitting electronic answers to questions in a medical form) and also received portable device data 24 for the same patient. System 42 compares each type of received data to determine whether the portable device data 24 corresponds to (e.g., matches or otherwise supports) the outcomes data. There may be a discrepancy or difference between the types of data, e.g., when a patient is reporting a positive outcome (e.g., good range of motion) but the portable device data 24 shows a poor outcome (e.g., a low range of motion). Generally, there is a difference or discrepancy among data when a value of one item of data differs from a value of another item of data. In this example, one type of data supports or corresponds to another type of data when a value of one item of data of one type matches (or substantially) matches a value of another item of data of the other type. In another example, there is a difference or discrepancy among data when a value of one item of data is within a specified range or threshold and a value of the other item of data is outside the specified range or threshold. In this example, there is a correspondence or supporting relationship among data when a value of one item of data is within a specified range or threshold and a value of the other item of data is inside the same specified range or threshold.

In an example, system 42 detects when there is a low outcome (e.g., to a procedure or implant). System 42 detects when there is a low outcome by executing a scoring rule that assigns various values to the patient's answers of an outcome form. System 42 aggregates these values to the answers to determine a score, an outcomes score. System 42 detects a low outcome by detecting an outcomes score that is outside a threshold or predefined range of acceptance scores. When system 42 detects a low outcome (or an outcome outside a predefined score or range), system 42 transmits a message or alert to the patient's portable that prompts the portable device to automatically collect a particular type of portable device data (e.g., pertaining to range of motion, mobility, etc.), e.g., when the portable device is online and connected to the Internet or network. The type of portable device data pertains to the area of the anatomy or physical attribute associated with the low outcome. Once collected, the portable device sends this collected data back to system 42 for validation and verification of the outcomes data.

In a variation, the alert or message is sent to the portable device, which has a direct communication channel with a patient's mobile device or personal computing device, enabling the mobile device to communicate with the portable device even when the mobile is offline. In another example, the alert transmitted to the portable device activates an application (e.g., an application for communication with system 42) on the patient's mobile device to cause the alert to display on the mobile device and to enable connection (e.g., via a URL in the alert) to system 42 over the Internet when the portable device is locally connected to the mobile device and the mobile device comes online. For example, after receiving the alert, the patient can connect the portable to the patient's mobile device or computer. The alert causes the patient's mobile device or computer to auto-launch the application provided by a service of system 42 to display the alert. When connected to the Internet, the patient may then click on the URL in the alert to use the application to access more detailed information about why the alert was generated and the outcomes data that caused the alert, or other information.

In this example, the alert could be an alert for the user to confirm the validity of the outcomes data or for the user to perform some motions or movements to enable the portable device (e.g., the sensors on the portable device) to detect certain physical attributes and to generate data indicative of those attributes for verifying the outcomes data. In this example, selection of the URL in the alert causes a display message to inform the patient of exactly which actions need to be performed.

In this example, system 42 updates a data record with the outcomes data in the database to include the portable device data 24 and/or overwrites the outcomes data with the portable device data 24. When the outcomes data is overwritten with the portable device data, the outcomes data is deleted to conserve system resources and enable increased processing speed (by reducing the amount of data that is processed during data analysis). The data is available on system 24 in real-time, at the moment data is being collected from the patient. When portable device data 24 supports or corresponds to the outcomes data 60, system 42 marks or tags outcomes data 60 as being validated or verified. When the outcomes data 60 is displayed in a GUI, system 42 modifies or updates the graphical user interface with an icon or other visualization to specify that the outcomes data is validated 60.

System 42 has more confidence in subjective, patient-reported data (i.e., the outcomes data) that has empirical evidence, such as the portable device data, to support it. And, for example, there will be comparable data-sets, subjective and objective, which could be mined to understand the psychology of outcomes reporting, and inform methods of improving the accuracy of patient-reported data. System 42 provides more data to inform clinician decision-making, and deliver better health outcomes for patients: better data, better, decisions, better outcomes. System 42 collects more accurate data (e.g., via the portable device data 24), to help inform clinician decision-making, and deliver better health outcomes to patients.

Under HIPAA rules, third party system 30 and system 42 are each obliged to seek permission to collect, store and share the patient's data (Protected Health Information). The data will be used solely for the purposes intended, namely to provide care of the patient. Third party system 30 obtains permission from the patient to collect data from wearables.

The data collected by wearables will be owned by third party system 30 and/or system 42. Access to the identifiable data will be managed by system 42 through a secure, permissions-based software system. The data stored in system 42 or data repository 50 can only be accessed by clinicians responsible for that patient's care, and trained staff. The data is not shared with any third party, except in cases permissible and required by HIPAA guidelines.

System 42 collects data from any wearable device which sends data to the cloud, and has an application program interface (API) service. API is a set of routines, protocols, and tools for building software applications. The API specifies how software components should interact and APIs are used when programming graphical user interface (GUI) components. Using a particular API for a particular wearable, system 42 is programmed to integrate with that API based on the routines and protocols for that API. Examples of wearable devices that system 42 is configured to integrate include, but not limited to: Fitbit, MisFit, Jawbone, Garmin. System 42 can integrate with any published API.

Figure 2:
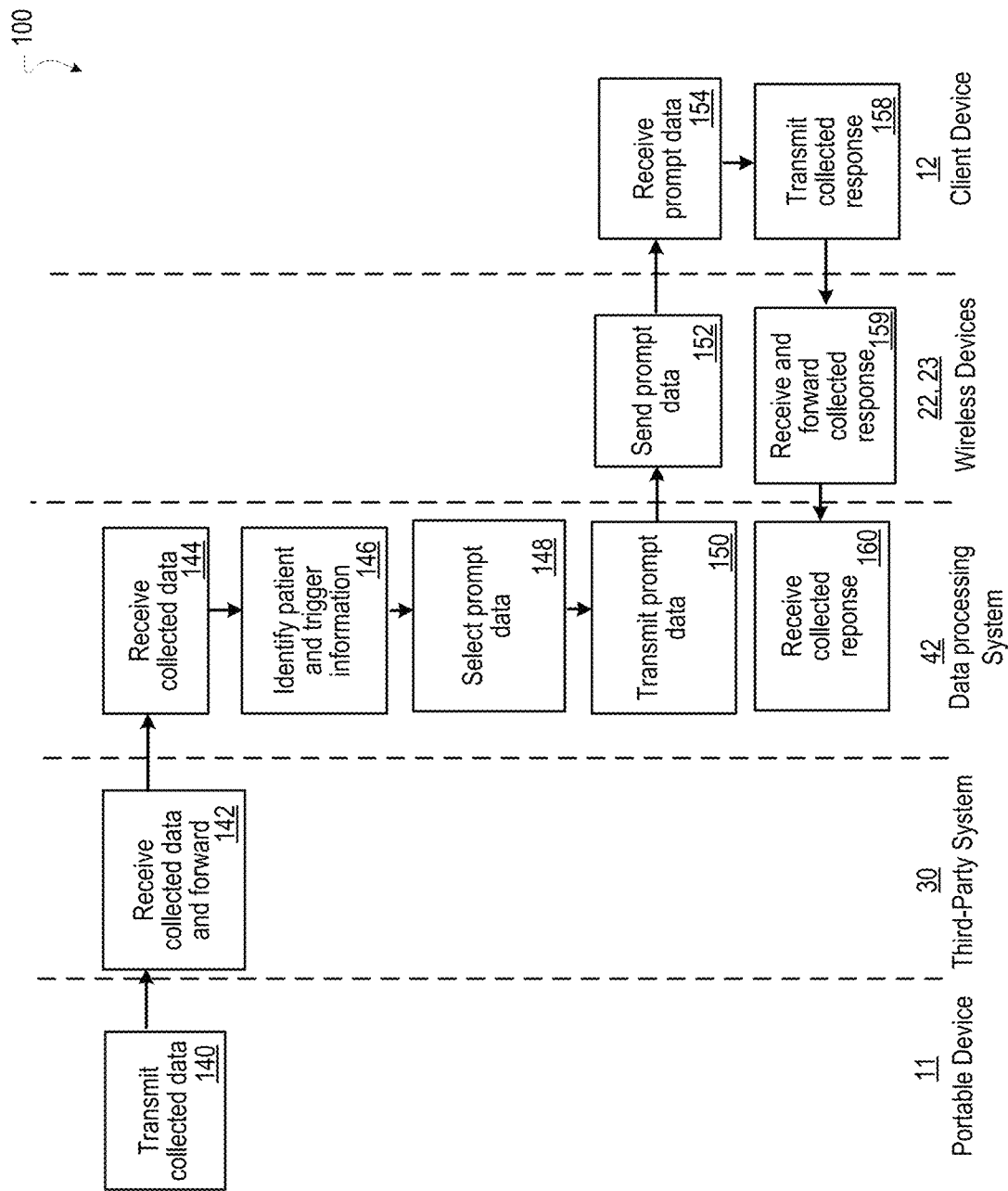
FIG. 2 shows an example of a flow diagram representing the dataflow through a data processing system.

FIG. 2 shows an example of a flow diagram representing the dataflow through the networked system 10. Operations performed by each device which handles data for the networked system 10 is represented by a column.

At step 140, the portable device 11 transmits portable device data 24 which has been collected by the portable device 11. The portable device data is transmitted using the network 20. At step 142, the third-party system 30 receives the portable device data 24. In some implementations the third party system 30 is configured to forward the portable device data at the first opportunity. In some examples, the third-party system 30 waits for the portable device data 24 to be requested by the networked system 10. In some examples, the third-party system 30 checks whether the networked system 10 has permission to access the portable device data 24 and does not provide the portable device data 24 until the networked system 10 has such permission.

The data processing system 42 receives the collected portable device data 24 at step 144. The portable device data 24 can be processed by the data processing system 40 or stored for later use in the data repository 50. At step 146, using the identifier in the portable device data 24, the data processing system 42 identifies the patient. The data processing system 42 can use the patient data profile 52 stored in the data repository 50 when analyzing the data. The patient can be associated with one or more candidate prompt data based on the information the patient's patient data profile 52. The one or more candidate prompt data can be customized by the medical service provider for a particular patient. For example, the medical service provider may designate one or more triggers related to one or more characteristics of the portable device data 24 based on the physical therapy regime recommended by the medical service provider such that the medical service provider can verify that the patient is following the physical therapy regime. The process of generating one or more customized candidate prompt data 32 is described in greater detail with respect to FIG. 3.

One or more characteristics of the portable device data 24, such as the patient identification and the type of measurement of patient activity received, are used to filter and select prompt data 32 at step 148. The data processing system 42 can filter data representing one or more prompts from a number of candidate prompts which are associated with the patient. The medical service provider can associate candidate prompts with the patient by designating metrics, triggers, and actions, which is described in more detail in relation to FIG. 3. The prompt data 32 can be selected based upon one or more characteristics of the portable device data 24, such as the type of measurement of physical activity or the values of the data. The prompt data is also selected based on selection of an appropriate question in an appropriate instrument, as described herein. In this example, data repository 50 stores information specifying associations between data indicative of questions and prompt data to enable system 42 to select an appropriate item of prompt data based on an associated question. Once the prompt is selected, the prompt data 32 is transmitted to the client device 12 based upon a destination address of the client device 12 when the client device is online using the network 20 at step 150. The one or more wireless devices 22, 23 send the prompt data to the client device 12 based upon the destination address of the client device 12 at step 152. Once the client receives the prompt data at step 154, the patient or a patient's representative responds to the prompt as appropriate. For example, the prompt data can include a question asking the patient to rate his or her pain levels on a scale of 1-10. The patient responds using the user interface 14 by entering a digit using a keypad, by setting a slider, by vocal indication, or other means of inputting the desired digit or response into the displayed instruction 16. The response is collected by the client device 12, which associates the responses to the patient using an identifier. Once the prompt has been answered, the client device 12 transmits (at step 158) the collected response data 28 using the network 20, such as the wireless devices 22, 23, which receives (at step 159) and forwards the collected response. The data processing system 42 receives (at step 160) the collected response data 28. The collected response data 28 can be analyzed by the data processing system 42, or stored in the data repository, such as in the patient profile data 52, for later use.

Figure 3:
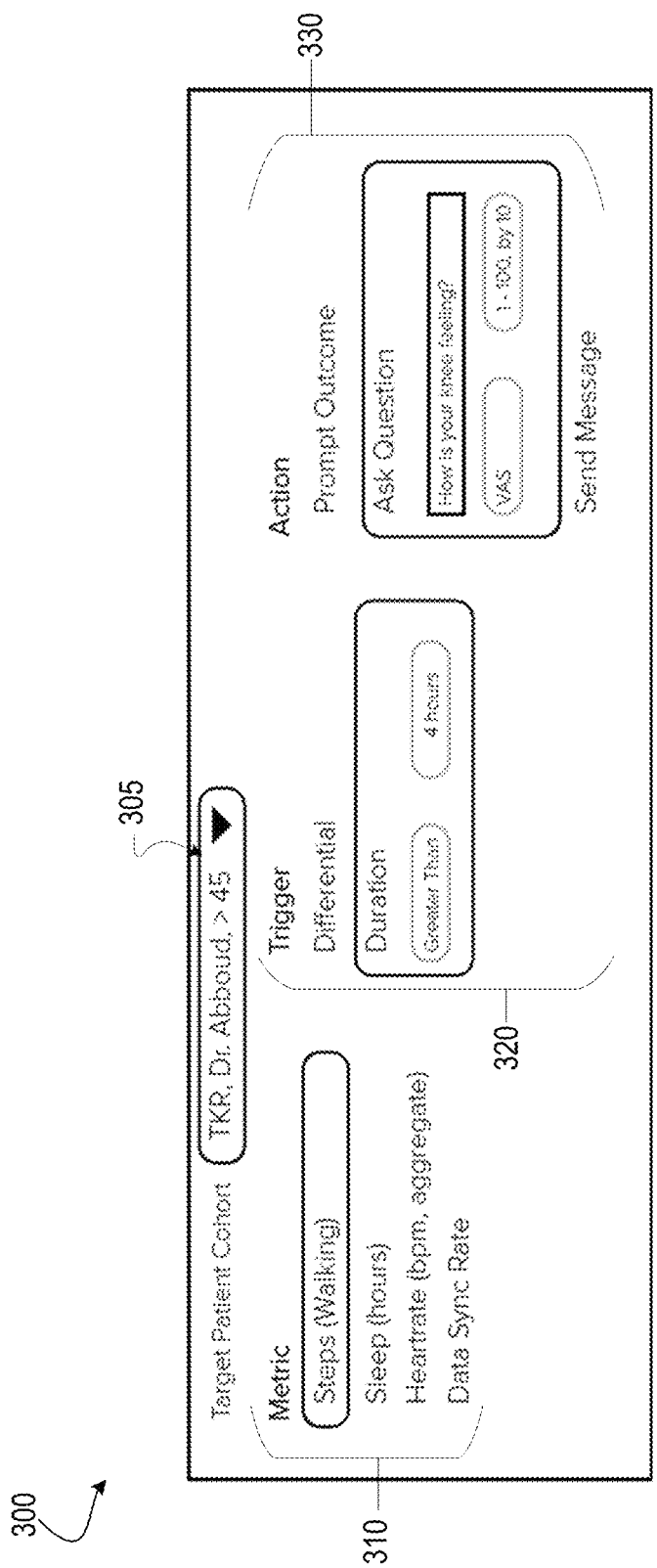
FIG. 3 shows an example of a graphical user interface.

FIG. 3 shows an example graphical user interface (GUI) 300 for generating candidate prompt data. The GUI 300 is used by a medical service provider to generate one or more candidate prompts (and rules) which can later be selected by the data processing system 42 to transmit to the client device 12 when applicable. For example, the GUI 300 could be accessed by a medical service provider through the clinician web portal. The medical service provider can prepare candidate prompt data prior to the data processing system 42 receiving the portable device data 24. In some examples, the medical service provider can create a library of candidate prompt data for a patient, group of patients, or class of patient for the data processing system 42 to filter through and select for transmission to the client device 12. For example, if the medical service provider desires to conduct a study on patients performing a particular therapy regime, the medical service provider can create a library of candidate prompt data for the identified patients.

The GUI 300 has a drop down menu 305 for selecting a target patient cohort. The target patient cohort includes types of patients who have characteristics meeting predefined criteria. For example, a patient can be selected for a target patient cohort depending on the patient's age, ailment, physician or other medical service provider, recent treatment, condition, diagnosis, or other characteristics. In FIG. 3, the target patient cohort are patients having Total Knee Replacement (TKR), who were operated or otherwise cared for by Dr. Abboud, and who are over the age of 45. Any combination of characteristics can be used to define a target patient cohort.

The GUI 300 is further divided into three main partitions (or portions) including the metric partition 310, the trigger partition 320, and the action partition 330. The metric partition 310 is used for designating a type of measurement of patient activity. The metric includes portable device data 24 characteristics such as number of steps (walking), number of hours of sleep, heartrate in beats per minute (BPM), calories burned, data sync rate, and other characteristics. The selected metric can later be used to determine whether the candidate prompt data is filtered out by the data processing system 42 or whether the candidate prompt data is selected to be transmitted to the client device 12.

The trigger partition 320 is used to designate the trigger used for determining whether to select and transmit the prompt data 32 to the client device 12 using the network 20. The trigger can be a threshold, differential, range of values, or other characteristic of the portable device data 24. In the GUI 300, the trigger includes a differential and time duration, where the time duration is greater than four hours. The trigger can be designated by activating buttons on the GUI and selecting the desired characteristics of the trigger. In this example, the trigger specifies a condition (e.g., walking for longer than 4 hours), the satisfaction of which causes data processing system 48 to execute an action, as specified in portion 330.

The action partition 330 is used to designate what action the patient should take upon receiving the prompt data 32 alert or notification. As previously described, the prompt data can require the patient to select, using the user interface 16, a URL sent to the client device 12 which specifies a location of a system for activating or viewing the action specified in portion 330. (In a variation, data indicative of the action specified in portion 330 is rendered on the client device independent of link selection). Once the link or notification has been activated, the action can require the patient to answer a question, fill out a form, rate pain, or otherwise submit response data 28 to the networked system 10. The action can activate an application on the client device 12 which causes the user interface 16 to display a question, form, or other action for the client to use to submit response data 28. The GUI shows an action including a prompt outcome. The prompt outcome is a question which is asked to the patient. The question asks how the patient's knee is feeling and invites a response of rating the pain from 1-100.

An example of using the generated candidate prompt data is as follows. The data processing system 42 can receive portable device data 24 which reports that a particular patient took over 2000 steps in less than four hours. The data processing system 42 can identify the patient and determine if there are any associated candidate prompts for the identified patient. If associated candidate prompt data exists, the data processing system 42 can select the prompt data 32. If the selected prompt data 32 has a trigger condition that has been met, such as that the patient walks over 200 steps in less than four hours, the data processing system 42 transmits the prompt data 32 to the one or more client devices associated with the identified patient. The transmitted prompt data 32 can include an alert. The alert can include a URL which specifies the location of the system for activating or viewing the prompt data 32. The prompt data 32 can activate a view application to cause the alert to display on the client device 12 and to enable connection via the URL to the networked system 10 over the internet when the wireless device is online. The URL can link to a questionnaire or an outcomes data question asking how the patient's knee feels. The patient can respond with response data 28 such as text reading "my knee hurts" or a numerical rating such as a 4 out of 10.

Figure 4:
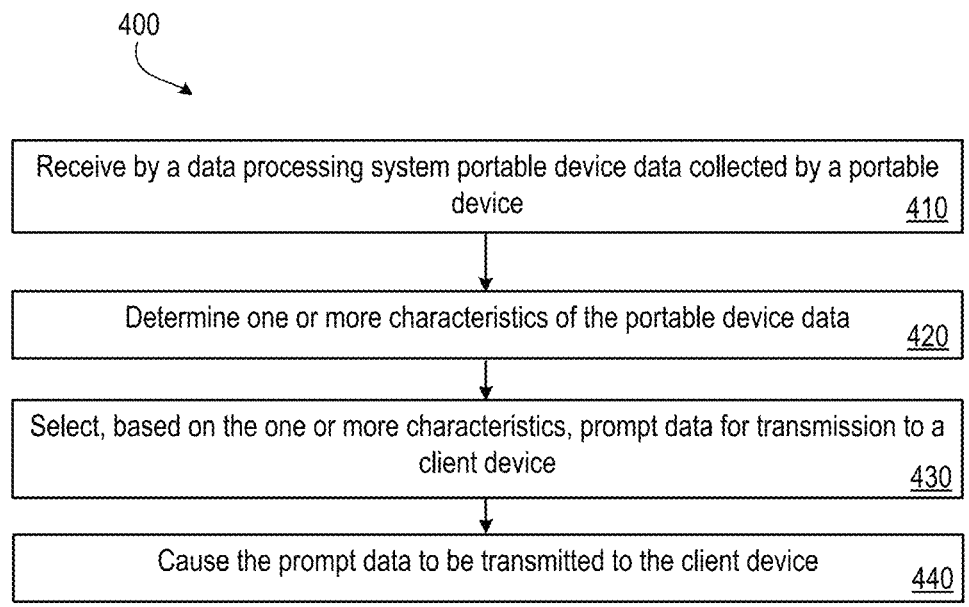
FIG. 4 shows an example of a process for processing portable device data.

FIG. 4 shows an example of a process for transmitting prompt data 32 to a client device 12. As described in detail with respect to FIGS. 1-2, the data processing system 42 receives (410) portable device data 24 collected from a portable device. The data processing system 42 determines (420) whether one or more characteristics of the portable device data 24 are associated with one or more candidate prompt data 32 and filters unassociated prompt data. If associated prompt data exists, the data processing system 42 selects (430) prompt data to transmit based on one or more characteristics of the prompt data, such as type of measured activity, values of the measured activity data, date, time, or identity of the patient. Once prompt data have been selected, the data processing system causes (440) the prompt data 32 to be transmitted to the client device 12. The prompt data 32 can include an alert. The prompt data 32 can generate a push notification for transmitting the prompt data 32 to the client device 12.

Figure 5:
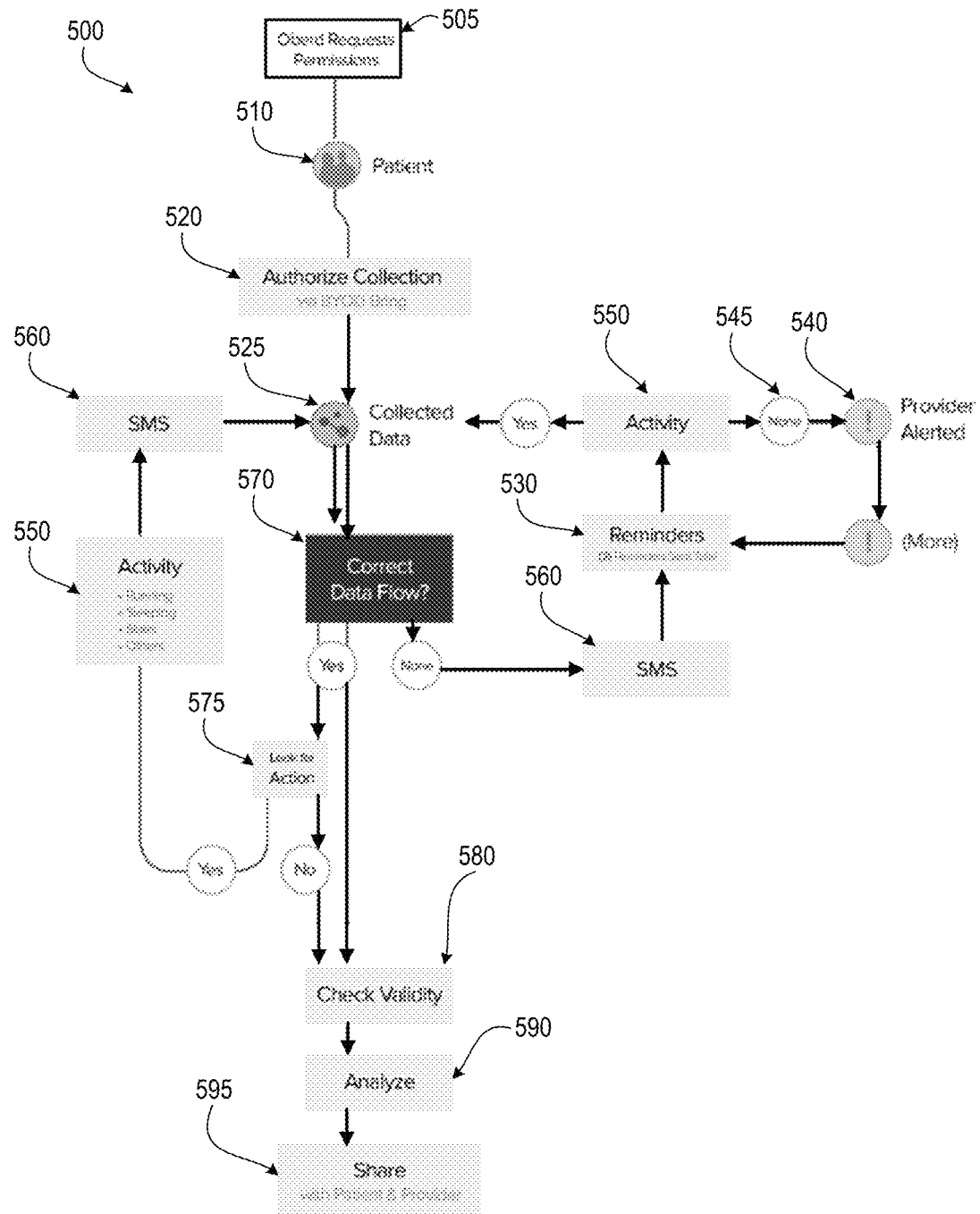
FIG. 5 shows an example of a diagram of a process for processing portable device data.

FIG. 5 shows an example process 500 for processing portable device data 24 using the data processing system 42 and the data processing program 40. The data processing system 42 requests permission 505 from the patient to access the portable device data 24 of the patient 510 from, for example, a third party system 30. The permission can be requested using the client device 12 and the patient web portal, or by using the clinician web portal at a location of the medical service provider (i.e., a hospital or physician's office). The permission can be acquired using a registration of the portable device 11 with the networked system 10, a registration of an associated third-party system 30 with the networked system 10, electronic consent using a messaging service, or direct consent on a patient web portal or the clinician portal by the patient 510.

The patient 510, having registered the portable device 11, can authorize collection of data such as response data 28 from client device 12 and portable device 11 associated with the patient using a "Bring Your Own Device" (BYOD) policy. A BYOD policy allows consumer devices to be integrated into the networked system 10.

The collected data 525 can be analyzed by the data processing system 42. A check is made to determine if there is proper data flow 570. The data processing system 42 can check to determine if a request for portable device data 24 has returned any data. The check can ensure that when a request for data is made the data processing system 42 receives a response. The check can ensure that the portable device 11 is synced to the networked system 10.

If data has not been received, the data processing system 42 can transmit a message to the client device 12 or repeat a request for portable device data 24. For example, the message can be an SMS message 560 sent to the client device 12 of a patient. In another example, the data flow can return no data because portable device data 24 has not been transmitted. The SMS message 560 can include reminders 530 to perform an activity send portable device data 24. The activity 550 can be an activity prescribed by a medical service provider for a therapy regime or any other type of patient activity which can produce portable device data 24. If no activity is detected 545, the medical service provider is alerted 540 and another reminder is sent 530. Reminders can be sent until activity is detected. A limit can be placed on the number of reminders which will be sent to a client device (e.g. three reminders). If an activity 505 is detected, the collected data is examined for correct data flow 570.

If the data flow 570 is correct, the process 500 can check for an action 575. The action can include a trigger. If an action is found, an activity is monitored. The activity can include one or more types of patient activity such as running, sleeping, climbing stairs, or other activity 550. A message 560 is sent with the portable device data 24 to the data processor 42. The data is collected 525 can checked for correct data flow 575.

If the data flow is correct and there are no more actions, the validity of the portable device data 24 is checked 580. In some examples, portable device data 24 is invalid if the portable device data 24 does not represent a physically possible or plausible scenario. For example, if the portable device data 24 suggests that a patient took one million steps in an hour, the portable device data 24 could be considered invalid. In another example, if the portable device data 24 suggests that the patient walked nonstop for two days, the portable device data could be considered invalid. Portable device data 24 that appears to have been improperly obtained and other "bad" data can be removed from the data set before the data is stored in the data repository 50 for further use.

Once the portable device data is deemed valid 580, the portable device data can be analyzed 590 to determine whether prompt data 32 should be transmitted from the data processing device 42 to the client device 12. The portable device data can be parsed using a rules engine 42a. The rules engine 42a can determine whether there are candidate prompt data which are associated with one or more characteristics of the portable device data 24. For example, if the portable device data includes data representing a number of steps taken, the rules engine 42a can determine that candidate prompt data which are associated with numbers of steps being taken should not be filtered out. The rules engine 42a can iteratively apply rules to the candidate prompt data associated with the patient until only associated candidate prompts remain. The rules engine 42a can then select one or more prompt data 32 to transmit to the client device 12 based on whether one or more trigger conditions are met.

After the data processing system 42 has determined whether to transmit prompt data 32, the data processing system 42 shares 595 the portable device data 24 with the patient, medical service provider, or both. The portable device data 24 can be stored in the data repository 50 for later use.

Figure 6:
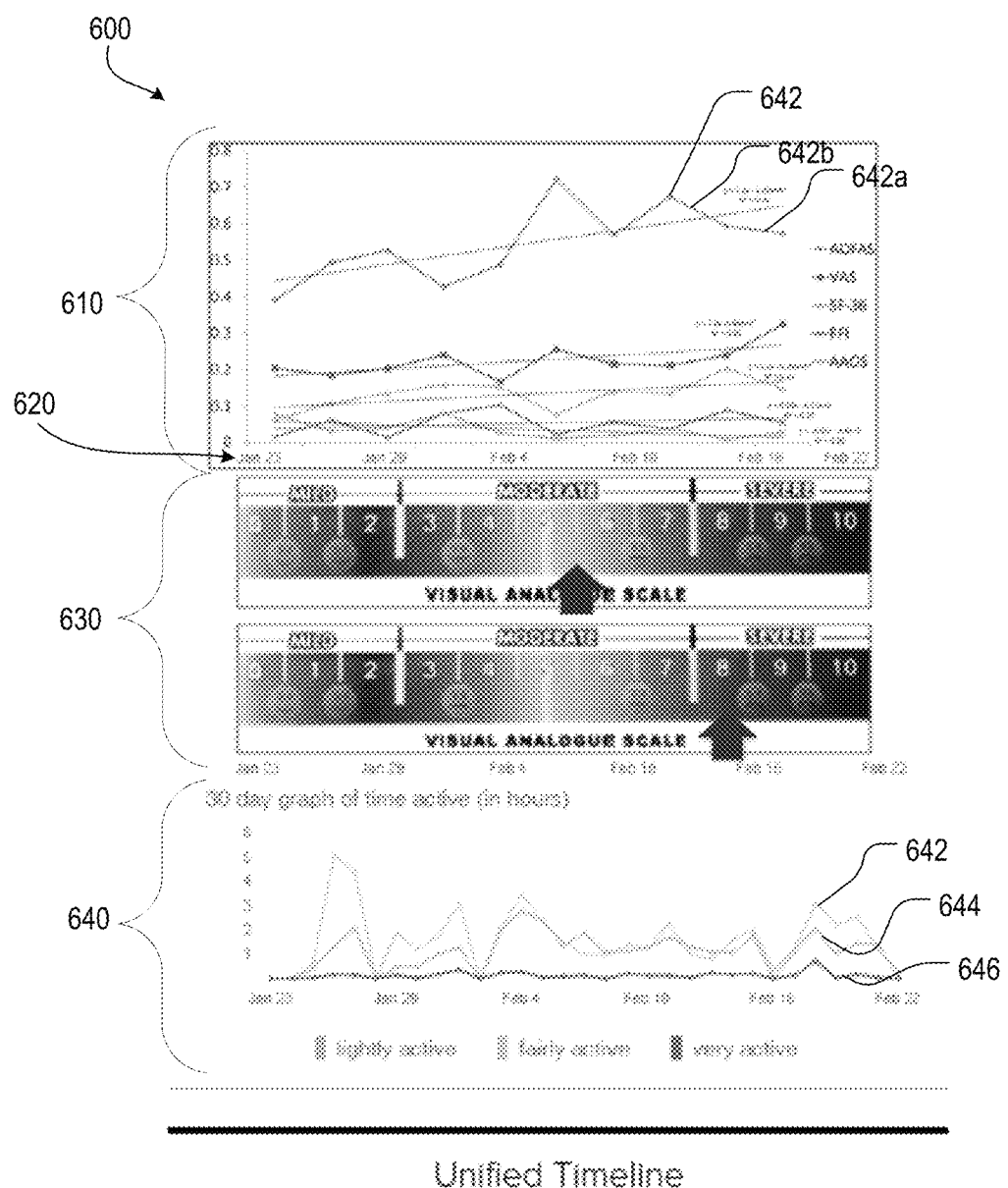
FIG. 6 shows an example of data visualization.

FIG. 6 is an example of data visualization 600. The example of data visualization 600 includes three partitions on a unified timeline 620. The unified timeline is a means of comparing the data presented for the three partitions. The first partition is the outcomes data partition 610. The second partition is the patient-defined outcomes partition 630. Generally, a patient-defined outcome is metrics that a patient specifies and then tracks results or metrics for that outcome. The third partition is the portable device data partition 640. Each of partitions 610, 630, 640 are juxtaposed to each other.

The outcomes data partition 610 shows outcomes data and scores for a patient and for a group of patients for a designated period of time (i.e. the unified timeline) for different outcomes instruments. The outcomes data and scores 60 of the patient can be compared to other patients in a patient cohort for one or more therapy regimes in a study, as specified in outcomes data and scores 68. For example, plot 642a illustrates the outcome scores for a particular patient over a specified period of time. Plot 642b illustrates average outcomes scores for a group of patients (answering questions to the same outcomes form that the patient represented in plot 642a answered) over the same time period. Variance in outcomes data and scores 60, 68 for many different patients of the same patient cohort can be compared, for example. FIG. 6 shows a graph having several outcomes data and scores 60, 68 for a given timeline (e.g. from January 23 to February 22).

The patient defined outcomes partition 630 shows response data metrics for a patient during the same timeline as the outcomes and scores data partition 610. In some examples, a large number of responses to a therapy regime can be collected. Some patients in a cohort with a particular ailment may rate their pain as being higher after a prescribed activity, than others. If many patients report high levels of pain, for example, the medical service provider can alter the therapy regime to reduce the activity required for the patients in the patient cohort, improving the quality of care.

The portable device data partition 640 can display portable device data for one or more patients in a patient cohort from during the unified timeline period. For example, the portable device data partition 640 can show for how many hours each day a patient was lightly active 642, fairly active 644, and very active 646. The patient and medical service provider can examine the portable device data partition to determine if a therapy regime is being followed or to determine what might be causing pain for the patient.

The unified timeline 620 allows the data from different partitions, and thus different sources, to be compared for the same timeframe. Outcomes data and scores 60, 68 can be compared to response data 28 and portable device data 24 over the same length of time. For example, a medical service provider can identify areas with low outcomes scores and quickly determine what measured physical activity might have caused the low outcome score 60. The outcomes data and score 60, 68 can be compared with the patient response data 28 to ensure that higher outcomes data scores 60, 68 actually represent more positive response data 28 from a patient.

FIG. 7 is a block diagram showing examples of components of networked system 10. Client device 12 can be any sort of computing device capable of taking input from a user and communicating over network 20 with system 42 and/or with other client devices. Client device 12 can be a mobile device, a desktop computer, a laptop, a cell phone, a personal digital assistant ("PDA"), a server, an embedded computing system, a mobile device and so forth.

System 42 can be a variety of computing devices capable of receiving data and running one or more services. In an example, system 42 can include a server, a distributed computing system, a desktop computer, a laptop, a cell phone, a rack-mounted server, and the like. System 42 can be a single server or a group of servers that are at a same position or at different positions (i.e., locations). System and client device 12 can run programs having a client-server relationship to each other. Although distinct modules are shown in the figures, in some examples, client and server programs can run on the same device.

System 42 can receive data from wireless devices 22, 23 and/or client device 12 through input/output (I/O) interface 190. I/O interface 190 can be a type of interface capable of receiving data over a network, including, e.g., an Ethernet interface, a wireless networking interface, a fiber-optic networking interface, a modem, and so forth. System 22 also includes a processing device 196 and memory 192. A bus system 194, including, for example, a data bus and a motherboard, can be used to establish and to control data communication between the components of system 22.

Processing device 196 can include one or more microprocessors. Generally, processing device 196 can include an appropriate processor and/or logic that is capable of receiving and storing data, and of communicating over a network (not shown). Memory 192 can include a hard drive and a random access memory storage device, including, e.g., a dynamic random access memory, or other types of non-transitory machine-readable storage devices. Memory 192 stores computer programs, such as the data processing program 40, which are executable by processing device 196. These computer programs include a rules engine 42*a* for implementing the operations and/or the techniques described herein. The rules engine 42*a* can be implemented in software running on a computer device, hardware or a combination of software and hardware.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible program carrier for execution by, or to control the operation of, a processing device. Alternatively or in addition, the program instructions can be encoded on a propagated signal that is an artificially generated signal, e.g., a machine-generated electrical, optical, or electromagnetic signal that is generated to encode information for transmission to suitable receiver apparatus for execution by a processing device. A machine-readable medium can be a machine-readable storage device, a machine-readable storage substrate, a random or serial access memory device, or a combination of one or more of them.

The term "processing device" encompasses all kinds of apparatus, devices, and machines for processing information, including by way of example a programmable processor, a computer, or multiple processors or computers. The apparatus can include special purpose logic circuitry, e.g., an FPGA (field programmable gate array) or an ASIC (application-specific integrated circuit) or RISC (reduced instruction set circuit). The apparatus can also include, in addition to hardware, code that creates an execution environment for the computer program in question, e.g., code that constitutes processor firmware, a protocol stack, an information base management system, an operating system, or a combination of one or more of them.

A computer program (which may also be referred to as a program, software, a software application, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or information (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input information and generating output. The processes and logic flows can also be performed by, and apparatus can also be implemented as, special purpose logic circuitry, e.g., an FPGA (field programmable gate array) or an ASIC (application-specific integrated circuit) or RISC.

Computers suitable for the execution of a computer program include, by way of example, general or special purpose microprocessors or both, or any other kind of central processing unit. Generally, a central processing unit will receive instructions and information from a read-only memory or a random access memory or both. The essential elements of a computer are a central processing unit for performing or executing instructions and one or more memory devices for storing instructions and information. Generally, a computer will also include, or be operatively coupled to receive information from or transfer information to, or both, one or more mass storage devices for storing information, e.g., magnetic, magneto-optical disks, or optical disks. However, a computer need not have such devices. Moreover, a computer can be embedded in another device, e.g., a mobile telephone, a smartphone or a tablet, a touch-screen device or surface, a personal digital assistant (PDA), a mobile audio or video player, a game console, a Global Positioning System (GPS) receiver, or a portable storage device (e.g., a universal serial bus (USB) flash drive), to name just a few.

Computer-readable media (e.g., one or more machine readable hardware storage devices) suitable for storing computer program instructions and information include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and (Blue Ray) DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back-end component, e.g., as an information server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital information communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In another example, the server can be in the cloud via cloud computing services.

While this specification contains many specific implementation details, these should not be construed as limitations on the scope of any of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for processing data in a data processing system, the method comprising:
   receiving, by the data processing system, a near real-time data stream of portable device data generated and transmitted by a wearable device independent of storing the stream of portable device data in a data repository;
   identifying, by the data processing system, a patient data profile stored in the data repository using an identifier in the stream of portable device data;
   obtaining, by the data processing system, data representing candidate time-sensitive prompt data based on the patient data profile;
   filtering, by the data processing system, the data representing the candidate time-sensitive prompt data by removing one or more items of the candidate time-sensitive prompt data that are unassociated with one or more characteristics of the stream of portable device data;
   based on the one or more characteristics of the stream of portable device data, selecting among the filtered data, by the data processing system, time-sensitive prompt data for transmission to the wearable device;
   generating, by the data processing system, an alert from the filtered, selected data, with the alert comprising a universal resource locator (URL), which specifies a location of a system for viewing the selected time-sensitive prompt data; and
   transmitting, by the data processing system, the generated alert to the wearable device, wherein the alert is configured to alert a wearer of the wearable device that the selected time-sensitive prompt data is ready for viewing, wherein the generated alert is configured to cause a client device associated with the wearable device to (i) activate a viewer application, (ii) enable connection to the system over the Internet, and (iii) obtain the selected time-sensitive prompt data for viewing in the activated viewer application.

2. The method of claim 1, further comprising:
   generating a push notification for transmitting the alert to the client device.

3. The method of claim 1, further comprising:
   binding values of one or more attributes included in the portable device data to one or more parameters of a rules engine;
   applying one or more rules to the bound parameters; and
   based on application of the rules, selecting the prompt data for transmission.

4. The method of claim 1, wherein the portable device data is received from a third party system.

5. The method of claim 1, wherein the method further comprises transmitting the prompt data to a third party system for transmission to the wearable device.

6. The method of claim 1, further comprising:
responsive to the prompt data, receiving outcomes data.

7. The method of claim 6, further comprising updating one or more entries in a data registry with the received outcomes data.

8. The method of claim 6, further comprising:
applying one or more rules to the received outcomes data; and
generating an outcomes score.

9. The method of claim 6, further comprising:
retrieving one or more of demographics data, satisfaction data, procedure data and implant data for a user associated with the received outcomes data; and
based on the retrieved data and the received outcomes data, determining an assessment of medical care for the user.

10. The method of claim 1, further comprising:
receiving consolidated clinical document architecture (CCDA) data from one or more external systems;
parsing the CCDA data to identify data associated with one or more predefined attributes;
identifying one or more users associated with the identified data; and
for the one or more identified users, identifying one or more portions of the portable device data pertaining to the one or more identified users, with the one or more portions of the portable device data specifying one or more specified characteristics of interest.

11. The method of claim 1, further comprising:
generating data for a graphical user interface that when rendered on a display device, renders a unified data visualization by displaying:
a first visualization of outcomes data over a specified time range;
a second visualization of patient defined outcomes data over the same specified time range; and
a third visualization of wearable metrics data over the same specified time range, with the first, second and third visualizations each being juxtaposed to each other.

12. One or more machine readable hardware storage devices storing instructions that are executable by one or more processing devices of a data processing system to perform operations comprising:
receiving, by the data processing system, a near real-time data stream of portable device data generated and transmitted by a wearable device independent of storing the stream of portable device data in a data repository;
identifying, by the data processing system, a patient data profile stored in the data repository using an identifier in the stream of portable device data;
obtaining, by the data processing system, data representing candidate time-sensitive prompt data based on the patient data profile;
filtering, by the data processing system, the data representing the candidate time-sensitive prompt data by removing one or more items of the candidate time-sensitive prompt data that are unassociated with one or more characteristics of the stream of portable device data;
based on the one or more characteristics of the stream of portable device data, selecting among the filtered data, by the data processing system, time-sensitive prompt data for transmission to the wearable device;
generating, by the data processing system, an alert from the filtered, selected data, with the alert comprising a universal resource locator (URL), which specifies a location of a system for viewing the selected time-sensitive prompt data; and
transmitting, by the data processing system, the generated alert to the wearable device, wherein the alert is configured to alert a wearer of the wearable device that the selected time-sensitive prompt data is ready for viewing, wherein the generated alert is configured to cause a client device associated with the wearable device to (i) activate a viewer application, (ii) enable connection to the system over the Internet, and (iii) obtain the selected time-sensitive prompt data for viewing in the activated viewer application.

13. The one or more machine readable hardware storage devices of claim 12, wherein the operations further comprise:
generating a push notification for transmitting the alert to the client device.

14. The one or more machine readable hardware storage devices of claim 12, wherein the operations further comprise:
binding values of one or more attributes included in the portable device data to one or more parameters of a rules engine;
applying one or more rules to the bound parameters; and
based on application of the rules, selecting the prompt data for transmission.

15. The one or more machine readable hardware storage devices of claim 12, wherein the portable device data is received from a third party system.

16. The one or more machine readable hardware storage devices of claim 12, wherein the operations further comprise:
transmitting the prompt data to a third party system for transmission to the wearable device.

17. The one or more machine readable hardware storage devices of claim 12, wherein the operations further comprise:
responsive to the prompt data, receiving outcomes data.

18. The one or more machine readable hardware storage devices of claim 17, wherein the operations further comprise:
updating one or more entries in a data registry with the received outcomes data.

19. The one or more machine readable hardware storage devices of claim 17, wherein the operations further comprise:
applying one or more rules to the received outcomes data; and
generating an outcomes score.

20. The one or more machine readable hardware storage devices of claim 17, wherein the operations further comprise:
retrieving one or more of demographics data, satisfaction data, procedure data and implant data for a user associated with the received outcomes data;
based on the retrieved data and the received outcomes data, determining an assessment of medical care for the user.

21. The one or more machine readable hardware storage devices of claim 12, wherein the operations further comprise:
receiving consolidated clinical document architecture (CCDA) data from one or more external systems;
parsing the CCDA data to identify data associated with one or more predefined attributes;
identifying one or more users associated with the identified data; and
for the one or more identified users, identifying one or more portions of the portable device data pertaining to the one or more identified users, with the one or more portions of the portable device data specifying one or more specified characteristics of interest.

22. The one or more machine readable hardware storage devices of claim 12, wherein the operations further comprise:
generating data for a graphical user interface that when rendered on a display device, renders a unified data visualization by displaying:
a first visualization of outcomes data over a specified time range;
a second visualization of patient defined outcomes data over the same specified time range; and
a third visualization of wearable metrics data over the same specified time range, with the first, second and third visualizations each being juxtaposed to each other.

23. A data processing system comprising:
one or more processing devices; and
one or more machine readable hardware storage devices storing instructions that are executable by the one or more processing devices to perform operations comprising:
receiving, by the data processing system, a near real-time data stream of portable device data generated and transmitted by a wearable device independent of storing the stream of portable device data in a data repository;
identifying, by the data processing system, a patient data profile stored in the data repository using an identifier in the stream of portable device data;
obtaining, by the data processing system, data representing candidate time-sensitive prompt data based on the patient data profile;
filtering, by the data processing system, the data representing the candidate time-sensitive prompt data by removing one or more items of the candidate time-sensitive prompt data that are unassociated with one or more characteristics of the stream of portable device data;
based on the one or more characteristics of the stream of portable device data, selecting among the filtered data, by the data processing system, time-sensitive prompt data for transmission to the wearable device;
generating, by the data processing system, an alert from the filtered, selected data, with the alert comprising a universal resource locator (URL), which specifies a location of a system for viewing the selected time-sensitive prompt data; and
transmitting, by the data processing system, the generated alert to the wearable device, wherein the alert is configured to alert a wearer of the wearable device that the selected time-sensitive prompt data is ready for viewing, wherein the generated alert is configured to cause a client device associated with the wearable device to (i) activate a viewer application, (ii) enable connection to the system over the Internet, and (iii) obtain the selected time-sensitive prompt data for viewing in the activated viewer application.

\* \* \* \* \*